(12) United States Patent
Kremeyer

(10) Patent No.: US 8,203,911 B2
(45) Date of Patent: Jun. 19, 2012

(54) ACOUSTIC AND OPTICAL ILLUMINATION TECHNIQUE FOR UNDERWATER CHARACTERIZATION OF OBJECTS/ENVIRONMENT

(76) Inventor: Kevin Kremeyer, Tucson, AZ (US)

( * ) Notice: Subject to any disclaimer, the term of this patent is extended or adjusted under 35 U.S.C. 154(b) by 316 days.

(21) Appl. No.: 12/289,261

(22) Filed: Oct. 23, 2008

(65) Prior Publication Data

US 2009/0103083 A1 Apr. 23, 2009

Related U.S. Application Data

(60) Provisional application No. 60/960,977, filed on Oct. 23, 2007.

(51) Int. Cl.
*G01H 9/00* (2006.01)
(52) U.S. Cl. .......................... 367/149; 367/128
(58) Field of Classification Search .................. 367/140, 367/141, 142, 149, 128; 356/317, 369; 73/601
See application file for complete search history.

(56) References Cited

U.S. PATENT DOCUMENTS

| | | | |
|---|---|---|---|
| 3,392,368 A | 7/1968 | Brewer et al. | |
| 7,260,023 B2 | 8/2007 | Jones et al. | |
| 2006/0096802 A1 | 5/2006 | Jones et al. | |
| 2009/0103083 A1* | 4/2009 | Kremeyer | 356/317 |
| 2009/0201763 A1* | 8/2009 | Jones et al. | 367/5 |

OTHER PUBLICATIONS

Kostli et al.; Optoacoustic tomography: time-gated measurement of pressure distributions and image reconstruction; Applied Optics / vol. 40, No. 22 / Aug. 1, 2001; pp. 3800-3809.*

Department of the Navy, U.S. Naval Research Laboratory, Correspondence dated Mar. 1, 2011 regarding patentability of U.S. Appl. No. 12/289,261 over U.S. Patent 7,260,023 to Jones et al.
Egerev, S. V. "In Search of a Noncontact Underwater Acoustic Source," *Acoustical Physics* 49:1 (2003) 51-61.
Jones, Theodore G. et al. "Laser-Generated Shocks and Bubbles as Laboratory-Scale Models of Underwater Explosions," *Shock and Vibration* 10 (2003) 147-157.
Kennedy, Paul K. "A First-Order Model for Computation of Laser-Induced Breakdown Thresholds in Ocular and Aqueous Media: Part I— Theory," *IEEE Journal of Quantum Electronics* 31:12 (Dec. 1995) 2241-2249.
Kennedy, Paul K. et al. "A First-Order Model for Computation of Laser-Induced Breakdown Thresholds in Ocular and Aqueous Media: Part II—Comparison to Experiment,"*IEEE Journal of Quantum Electronics* 31:12 (Dec. 1995) 2250-2257.
Michel, Anna P.M. et al. "Oceanic Applications of Laser Induced Breakdown Spectroscopy: Laboratory Validation," *Oceans* 2005, vol. 1 (Sep. 2005) 741-747, IEEE Catalog No. 05CH37711.
Mullen, Linda J. "Hybrid Lidar-Radar Ocean Experiment," *IEEE Transactions on Microwave Theory and Techniques* 44:12 (Dec. 1996) 2703-2710.
Sacchi, C. A. "Laser-Induced Electric Breakdown in Water," *J. Opt. Soc. Am. B* 8:2 (Feb. 1991) 337-345.
Siegman "Pulse Propagation in Nonlinear Dispersive Systems," *Lasers*, Chapter 10 (1986) 375-386.
Sprangle, P. et al. "Propagation of Intense Short Laser Pulses in the Atmosphere," *Physical Review E* 66 (2002) 046418.
Strand, Michael P. "Underwater Electro-Optical System for Mine Identification," *SPIE* 2496 (1995) 487-497.

(Continued)

*Primary Examiner* — Daniel Pihulic
(74) *Attorney, Agent, or Firm* — Jones Day

(57) ABSTRACT

The invention provides a method for acoustically and optically characterizing an immersed object of interest by generating a serial plurality of acoustic and optical illumination pulses through a liquid. In addition to the spectral analyses/imaging of objects/environment made possible by the white-light illumination, a target material can be ablated, generating an ionized plume to spectrally identify the target's constituent atoms.

31 Claims, 7 Drawing Sheets

OTHER PUBLICATIONS

Vogel, A. et al. "Shock Wave Emission and Cavitation Bubble Generation by Picosecond and Nanosecond Optical Breakdown in Water," *J. Acoust. Soc. Am.* 100:1 (Jul. 1996) 148-165.

Zevallos, Manuel E. et al. "Time-Gated Backscattered Ballistic Light Imaging of Objects in Turbid Water," *Applied Physics Letters* 86 (2005) 011115.

* cited by examiner

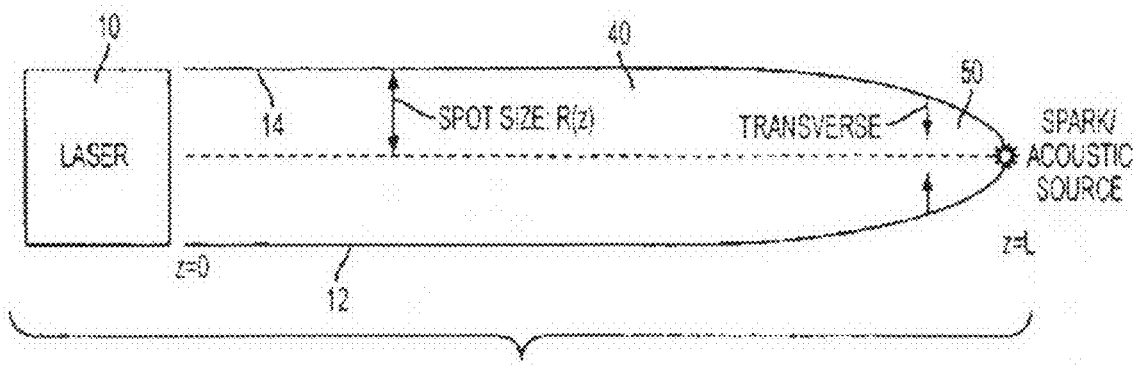
FIG. 1A
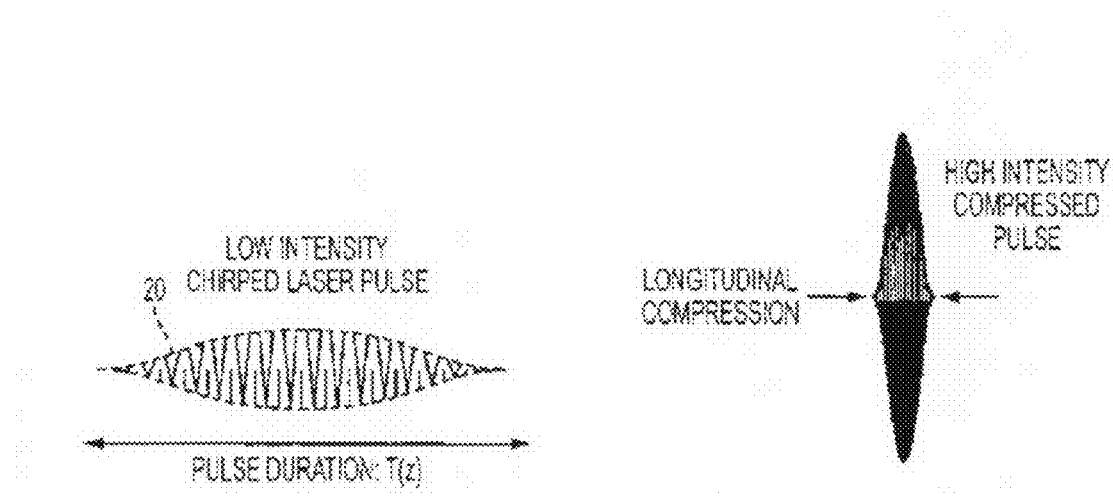
FIG. 1B
FIG. 1C

ACOUSTIC AND OPTICAL ILLUMINATION TECHNIQUE FOR UNDERWATER CHARACTERIZATION OF OBJECTS/ENVIRONMENT

CROSS REFERENCE TO RELATED APPLICATION

This application claims the benefit of priority from U.S. Provisional Patent Application No. 60/960,977, filed Oct. 23, 2007. The U.S. provisional application, in its entirety, is incorporated herein by reference.

The following patents and patent applications are each incorporated herein by reference in their entirety:
1) U.S. Pat. No. 6,527,221, which granted on Mar. 4, 2003, entitled "Shockwave Modification, Method and Apparatus and System;"
2) U.S. Pat. No. 7,063,288, which granted on Jun. 20, 2006, entitled "Shockwave Modification, Method and System;"
3) U.S. Pat. No. 7,121,511, which granted on Oct. 17, 2006, entitled "Shockwave Modification, Method and System;"
4) U.S. patent application Ser. No. 11/288,425 filed on Nov. 29, 2005, now U.S. Pat. No. 7,648,100, and entitled "Shockwave Modification, Method and System;"
5) U.S. patent application Ser. No. 11/540,964 filed on Oct. 2, 2006 and entitled "Shockwave Modification, Method and System;" and
6) U.S. patent application Ser. No. 12/733,252, filed on Feb. 19, 2010, which is the National Phase of International Patent Application No. PCT/US2008/009885 filed on Aug. 20, 2008 and entitled "Energy-Deposition Systems, Equipment and Methods for Modifying and Controlling Shock Waves and Supersonic Flow."

BACKGROUND OF THE INVENTION

Self-focusing/compressing ultrashort pulse lasers are employed to generate acoustic and light sources that can acoustically, optically, and spectrally characterize underwater objects and environments and also be used to transmit data. The disclosed technology comprises a technique to characterize undersea objects and environments in ways that have never before been possible. The technique combines very short acoustic and optical pulses which provide broadband "illumination" over the full white light optical spectrum, as well as over a very broad acoustic range, up to several Megahertz. In addition to the spectral analyses/imaging of objects/environment made possible by white-light illumination, a target material can be ablated, generating an ionized plume to spectrally identify the target's constituent atoms. This approach combines a number of cutting edge technologies, each of which has been demonstrated to some extent in different environments or with different laser pulses. As a result, although the technologies are complex and involve extension into new regimes, each element is grounded in past experiments, and it is their combination here and application in new environments that constitutes the primary advance.

Characterization of the environment and objects is often performed using acoustic-imaging techniques which involve "illuminating" the targeted scenes with large amounts of acoustic energy, centered around relatively low frequencies, with relatively narrow bandwidths. Optical characterization can also be performed, but again typically requires large amounts of illumination energy, especially considering the stronger attenuation in the ocean of optical energy than acoustic energy. There are several problems with illuminating the undersea environment with large amounts of energy. From a militarily tactical perspective, this practice generates a strong signature, advertising the illuminator's presence and allowing adversaries to much more easily detect, and then evade and/or find them. From an environmental perspective, depositing large amounts of energy into the ocean can damage the sea life/environment, resulting in unwanted effects and repercussions. A further technological advantage is that the broadband, short acoustic and optical pulses will allow much greater resolution than the relatively long and narrow-band illumination pulses currently employed. Rastering high repetition-rate pulses to form a spatial array will allow for yet greater acoustic resolution, while time-gating the measured return signals (acoustic and/or optical) will provide much greater spatial resolution and penetration through turbid waters.

Combining ultrashort pulse lasers and short-gate imaging, Zevallos et al. have demonstrated the ability to resolve images through murky scattering environments, which were formerly completely impenetrable using any other optical means (Manuel E. Zevallos L., S. K. Gayen, M. Alrubaiee, and R. R. Alfano, "Time-gated backscattered ballistic light imaging of objects in turbid water", Appl. Phys. Lett. 86, 011115 (2005)). Employment of femtosecond continuums adds a spectral element, not only allowing additional diagnostics (by seeing the spectrally-resolved return signals), but also ensures the presence of the least attenuated wavelength(s) for any given environment, exceeding those of state-of-the-art underwater LIDAR systems, which employ longer, monochromatic laser pulses. The shorter acoustic and optical pulse widths can enable increases in resolution of up to three orders of magnitude, and the increased penetration capability and time-gated imaging is anticipated to increase range by at least one to two orders of magnitude. The materials discrimination capabilities, made possible by laser-induced breakdown spectroscopy (A. Michel, M. Lawerence-Snyder, S. M. Angel, A. D. Chave "Oceanic Applications of Laser Induced Breakdown Spectroscopy: Laboratory Validation", 2005 IEEE/MTS Annual Meeting); comparison of differently-filtered images, and biomimetic signal processing of broadband acoustic return signals, is a yet further benefit, which will allow an entirely new capability in target identification/discrimination.

Mullen et al. (L. J. Mullen, P. R. Herczfeld, and V. M. Contarino, IEEE Trans. Microwave Theory Tech. 44, 2703 (1996)) and Strand et al. (M. P. Strand, in Detection Technologies for Mines and Minelike Targets, edited by A. C. Dubey, I. Cindrich, J. M. Ralston, and K. Rigano [Proc. SPIE 2496, 487 (1995)]) have clearly articulated the need for new technologies to increase range and resolution in performing shallow-water surveying and underwater mine detection in turbid waters. The effectiveness of the employed techniques determines which waters can and cannot be mapped/characterized in advance, and once in a given environment, the ability to detect and characterize dangers ahead of a craft places constraints on speed and the ability to maneuver. Positive identification of obstacles is furthermore required to eliminate the need to treat debris the same way one treats a mine. Beyond operation in the field, the need for these capabilities is further required to help counter the increasing asymmetric threat coming from terrorist activities both abroad and at home. If the proposed approach increases range, resolution, and certainty by one to three orders of magnitude, it will allow a vehicle to proceed more quickly by the same amount when probing for dangers. For example, a 10-fold increase will allow an increase from 3 knots to 30 knots, which is operationally very significant. These capabilities are of great interest to both the United States Coast Guard and the United States Navy, as well as to merchant, commercial, and private vessel operators.

The disclosed illumination approach addresses a number of current operational problems faced by the military, including characterization of the littoral environment and identification of mines, unexploded ordnance, and environmental impact/effects. This optical and acoustic characterization is of particular importance in submarine situational awareness, since it will provide high quality imaging and enhancement of collision avoidance capability. Targeted high-resolution acoustic imagery is often difficult to obtain in a complex environment, and optical characterization can be difficult or impossible to obtain with monochromatic sources and especially in turbid waters. A direct benefit of the disclosed technique will be enhanced remote sensing/detection of ordnance in near-shore locations. A further benefit of the spectral aspect of the technology is its potential use as a tool by both the US Navy and Coast Guard for pollution/HAZMAT prevention and response decision. Not only will the spectral analysis ability help in material identification, but it can also be coupled to software and databases for automation of this task.

The claimed technology is a multifaceted tool to address several problems, which are currently approached in a number of ways. Identification of chemicals is often done through water sampling and chemical analysis, which is a time-consuming and cumbersome process. Identification of a target material is often done through visual imagery and assessment of the material's acoustic impedance-mismatch with water. This can be an uncertain process and is susceptible to deception techniques. In many cases, positive identification requires close proximity to the target, with the best diagnosis involving the deployment of a diver. However, close proximity of divers and assets is undesirable when assessing the nature of a given target object. Maintaining a large stand-off distance and illuminating the object with white light and acoustic energy currently requires a large flash and loud ping. However, the nature of maritime scatterers tends to diffuse this input energy and "blur" the final results.

Another approach to characterizing targets and the maritime environment is to obtain spectral information. Performing these measurements on the water column allows the assessment of its chemical content, however conventional means to acquire spectral information require either direct sampling or a remote white light source that points through the targeted medium to a spectrometer. These approaches can be time-consuming and risky because of the proximity of either a vehicle and/or tether. Direct spectral analysis of a solid target using conventional techniques also requires physical contact with the target. Again, this is inherently dangerous, and the identified concerns in these prior capabilities are obviated through the disclosed method.

The coupling of electromagnetic/optical probing techniques to acoustic signals presents the potential to decouple the observer from the water, which has sparked significant interest and extensive research. One current worldwide effort is to increase the Maritime Domain Awareness. An important goal for this program is to develop passive acoustic sensors which can be liberally deployed, measure a wide range of signals, and require little to no power or maintenance. Employing optical techniques to probe the acoustic environment represents an approach with many benefits, in that signals can be emitted and measured from outside the water, without depending on assets in the water. Two of the key organizations involved in this effort are the U.S. Coast Guard (USCG) and the National Oceanic and Atmospheric Administration (NOAA). Their interest in this application is further reason to pursue the investigation of coupled optical and acoustic measurements.

The ability to remotely create an acoustic signal in the water has been investigated using both continuous wave and pulsed lasers by a number of Department of Defense (DoD) agencies. The Naval Undersea Warfare Center—Newport Division has worked on developing laser acoustic source and detection schemes at the ocean surface in order to communicate with undersea vehicles. Their approach allows for minimal air propagation, requires lens focusing, and takes advantage of neither underwater optical propagation nor the remote optical compression enabled by ultrashort pulse lasers. Their modulated continuous wave laser acoustic source arrays at the ocean surface also do not benefit from underwater laser propagation. The methods furthermore yield undesirably low efficiencies and weak acoustic signals because the mechanism to generate acoustic signals when using low laser intensities involves heating instead of optical breakdown. To investigate the benefits of optical breakdown, the Naval Research Laboratory (NRL) has had several groups investigate this technique to generate acoustic signals using high-intensity pulsed lasers. Certain groups have investigated short-pulse lasers (nanoseconds) with pulse energies exceeding 100 Joules (J), while other groups have investigated ultrashort laser pulses (sub-picosecond pulses) with millijoules (mJ) of energy per pulse. Their acoustic results are sufficiently pertinent that we have included some of them in the descriptions of section B. They have recently received a U.S. Pat. No. 7,260,023 for the generation of acoustic signatures using non-linear self-focusing, with an ongoing application (20060096802).

S. V. Egerev describes development of noncontact laser acoustic sources in "In Search of a Noncontact Underwater Acoustic Source", Acoustical Physics, vol. 49, issue 1, pages 51-61, 2003. A laser-based ultrasonic and hypersonic sound generator is discussed in U.S. Pat. No. 3,392,368 to Brewer et al. Laser induced electric breakdown in water is discussed by C. A. Sacchi in the Journal of the Optical Society of America B, Vol. 8, No. 2, February 1991, pages 337-345. P. K. Kennedy discusses laser induced breakdown thresholds in ocular and aqueous media in IEEE Journal of Quantum Mechanics, Vol. 31, No. 12, December 1995, pages 2241-2249 and 2250-2257. A. Vogel and S. Busch discuss shock wave emission and cavitation generation by picosecond and nanosecond optical breakdown in water in J. Acoustical Society of America, Vol. 100, Issue 1, July 1996, pages 148-165.

T. G. Jones, J. Grun, L. D. Bibee, C. Manka, A. Landsberg, and D. Tam discuss laser-generated shocks and bubbles as laboratory-scale models of underwater explosions in Shock and Vibration, IOP Press, Vol. 10, pages 147-157, 2003.

P. Sprangle, J. R. Penano, and B. Hafizi discuss propagation of intense short laser pulses in the atmosphere in Physical Review E, Vol. 66, 2002, pages 046418-1-046418-21. The optical Kerr effect, a non-linear change in the refractive effect at high intensity, is discussed by Siegman, Lasers, pages 375-386, 1986.

BRIEF SUMMARY OF THE INVENTION

A method employing ultrashort pulse lasers to generate acoustic and optical sources to characterize the marine environment and underwater targets allows far more benefits than simply the creation of an acoustic pulse. The disclosed technology combines optical interrogation techniques with the previously-explored acoustic measurement. The optical techniques include the ability of ultrashort laser pulses to generate a white light continuum for imaging, as well as generate a spectral signature from laser-induced spectroscopy (LIBS) at the target surface. The optical measurements can also be time-gated to select only the return pulse from the desired target. This requires knowledge of the distance to the target, which can be determined from the acoustic echo-time. Any one of these approaches has potentially great benefits, and their combination will provide yet greater flexibility in developing applications and solutions to existing problems. The disclosed system simultaneously takes advantage of as many of the ultrashort pulse laser effects as possible. The very short and broad-band optical and acoustic pulses we generate will allow much higher resolutions to be achieved in both optical and acoustic imaging over conventional methods. Our goal is to couple these abilities, along with the related spectral identification/characterization techniques, to develop a powerful new tool, capable of high-fidelity acoustic and optical imaging through turbid water, as well as remote material identification.

Embodiments entailing generating an acoustic and optical source in a liquid, the method comprising: transmitting an optical pulse through the liquid; the optical pulse reaching and/or exceeding the intensity required for laser induced breakdown of the liquid ($I_{LIB}$) through pulse compression and ionizing a liquid volume, thereby generating an acoustic pulse, wherein the pulse compression is achieved through at least one of optical group velocity dispersion induced longitudinal compression of a frequency chirped optical pulse and transverse self focusing via a nonlinear optical Kerr effect.

Another embodiment of the invention is directed to a method for generating a series of acoustic and optical illumination sources in a liquid, the method comprising: generating and transmitting a plurality of optical pulses through the liquid; the optical pulses reaching $I_{LIB}$ through pulse compression and ionizing a liquid volume, thereby generating a plurality of acoustic pulses and/or sources and optical illumination sources, wherein the pulse compression is achieved through at least one of optical group velocity dispersion induced longitudinal compression of a frequency chirped optical pulse and transverse self focusing via a nonlinear optical Kerr effect; and steering each optical pulse with a reflective surface.

Pulse compression can include both optical group velocity dispersion induced longitudinal compression of a frequency chirped optical pulse and transverse self focusing via a nonlinear optical Kerr effect.

The liquid can have a positive or negative optical group velocity dispersion parameter $\beta_2$, and the optical pulse can have a corresponding negative or positive frequency chirp. In some embodiments, the optical pulse has a wavelength varying with time, including, but not limited to varying linearly in time. In other embodiments, the optical pulse can be a monochromatic optical pulse or a broadband optical pulse without chirp.

BRIEF DESCRIPTION OF THE DRAWINGS

FIG. 1A is a schematic view of a method for remotely generating an acoustic and optical illumination source according to an embodiment of the invention.

FIG. 1B illustrates a negatively chirped optical pulse before propagation.

FIG. 1C illustrates the optical pulse of FIG. 1B after propagation and longitudinal compression.

DETAILED DESCRIPTION OF THE PREFERRED EMBODIMENTS

Figure 3:
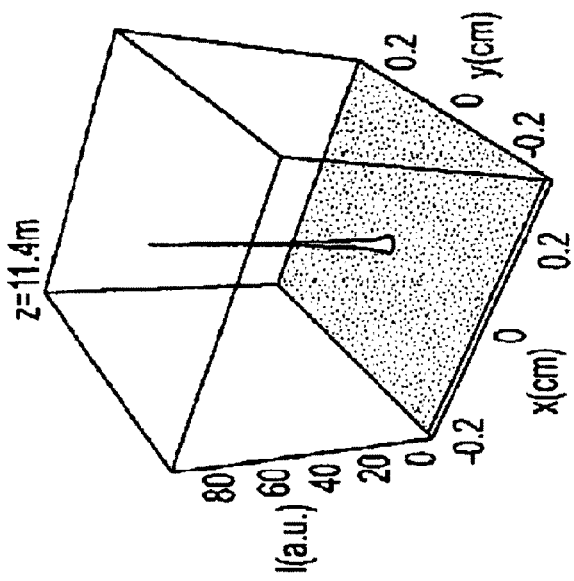
FIG. 3 shows the calculated intensity of a laser generated optical pulse of FIG. 2 after a computer simulation of propagation through water, according to an embodiment of the invention.

The method for remotely generating a combined acoustic and optical illumination source in water or another liquid having optical group velocity dispersion occurs through multiple mechanisms. The acoustic source is generated through a photo-acoustic sound generation technique, capable of generating an acoustic pulse at a predetermined remote underwater location many meters from the laser source. The remote acoustic generation occurs in two phases: 1) underwater laser pulse propagation and compression using some combination of group velocity dispersion-induced longitudinal compression, and transverse focusing due to the nonlinear refractive index of the liquid, and 2) laser-induced breakdown, heating and vaporization of a liquid volume, followed by rapid expansion and generation of a shock wave that can serve as a useful acoustic pulse. The concurrently generated optical illumination source arises through several potential mechanisms, including but not limited to: incoherent line emission and scattering from the generated plasma; emission of white light, such as conical emission and/or emission from self-phase modulation, either with or without significant plasma generation; coherent light passing through and/or refracting through the generated plasma; coherent and incoherent light shifted from the original laser wavelength also propagating through, refracting through, or scattering through/from the generated plasma.

FIGS. 1A-1C illustrate schematically the system and method for remotely generating an acoustic and optical illumination source according to one or more embodiments of the invention. A laser source 10 generates an optical pulse 20. The optical pulse 20 travels a distance in the water or other liquid having group velocity dispersion, characterized by the parameter $\beta_2$. The optical pulse is transversely and/or longitudinally compressed as it travels, until the intensity of the pulse is sufficient to cause laser induced breakdown. The propagation paths of the outer edges of the optical pulse are depicted by two solid lines 12 and 14, showing potential non-linear Kerr self-focusing of the pulse. The pulse can simultaneously undergo longitudinal compression due to group velocity dispersion.

The wavelength of the laser is preferably selected to be a wavelength having a low attenuation in the water or other desired liquid, as attenuation can be a strong function of the wavelength $\lambda$. Attenuation of light in water can be characterized by an attenuation length $L_{atten}$, with the beam intensity decreasing with propagation distance z according to $I(z)=I(0) \exp(-z/L_{atten})$. In pure water, maximum transmission (and minimum absorption) occurs generally in a wavelength range of 300-500 nanometers, with a maximum attenuation length in this range of approximately 50 meters. For sea water, the attenuation length, $L_{atten}$, is a function of impurity concentrations, with typical values of 5 to 10 meters. The global average $L_{atten}$ is approximately 4 meters, and for relatively clear ocean water $L_{atten}$ can be 10 meters or greater. For embodiments in which the maximum energy is required at the acoustic source, the propagation path length should be selected to be less than $L_{atten}$. For applications requiring lower energy, the total underwater propagation path can be a few times greater than the attenuation length.

For optimal transmission in water, the wavelength $\lambda$ of the optical pulse can be between about 300 nm and 500 nm, or 260 nm to 650 nm. In one embodiment, a commercially available broadband ultrashort pulse laser of wavelength range somewhere between roughly 740-810 nm generates pulses of duration between roughly 20 to 120 femtoseconds, and a frequency doubling crystal converts a portion of the energy to a wavelength range somewhere roughly between 370-405 nm. In another embodiment, an Nd-doped laser produces pulses of duration between roughly 2-10 nanoseconds at a wavelength in the range of 1050-1070 nanometers, and a frequency doubler converts a portion of the energy to a 525-535 nm wavelength.

Although not thusly limited, the pulse 20 is preferably frequency chirped, with its wavelength and frequency being a function of time. For liquids such as water, where $\beta_2$ is positive, the pulse must be negatively frequency chirped, so that the pulse has a shorter wavelength at the head of the pulse and a longer wavelength at the end of the pulse. Such a negatively chirped pulse in a liquid having a positive $\beta_2$ will compress longitudinally as it propagates. Although not thusly limited, for a liquid with linear group velocity dispersion, the wavelength of the pulse should be a linear function of time to achieve optimal longitudinal pulse compression.

The chirped pulse can be generated by optical grating-based dispersion such as that occurring in a chirped pulse amplifier laser, or by any suitable dispersion method.

Longitudinal compression of the optical pulse as it travels through the liquid relies on the group velocity dispersion (GVD) parameter of the liquid, $\beta_2$. The GVD parameter, $\beta_2$, is proportional to the rate of change of group velocity of light with wavelength $d\nu_g/d\lambda$ over a range of frequencies, and is positive for water. Therefore, in water, the light with a longer wavelength travels faster than light with a shorter wavelength. For an optical pulse with negative frequency chirp, the initial shorter wavelength portions of the optical pulse travel slower through the liquid than the later, longer wavelength portions. The pulses are thus longitudinally compressed, so the pulse duration is shortened as the optical pulses travel through the liquid. For a negatively chirped pulse in which the wavelength of the pulse is a linear function of time in a medium with linear GVD, the propagation distance $L_{GVD}$ needed to produce maximum longitudinal pulse compression is approximately equal to $T(0)/\beta_2 \Delta\omega$, where $T(0)$ is the initial pulse duration and $\Delta\omega$ is the frequency bandwidth. Control and variation of the initial pulse length $T(0)$ and/or the laser bandwidth $\Delta\omega$ provides control of the of the longitudinal compression range.

As the pulse duration is shortened through the longitudinal compression, the intensity of the pulse increases, as illustrated in FIG. 1C.

Transverse compression of the pulse occurs generally when the optical intensity of the pulse is sufficiently high to induce nonlinear optical effects (for example, nonlinear self focusing or NSF). The threshold intensity above which non-linear optical effects are induced is represented by $P_{NSF} = \lambda^2/2\pi n_0 n_2$, where $n_0$ is the linear index of refraction and $n_2$ is the nonlinear index of refraction, and an approximation of the overall index of refraction to the lowest order in the pulse intensity is $n = n_0 + n_2 I$. As an example, for light with a wavelength of 400 nm, $P_{NSF}$ is on the order of 1 megawatt in water.

In light with high intensities (light with power above $P_{NSF}$), the intensity excites a significant nonlinear response of the refractive index (the Kerr optical effect). The nonlinear refractive index induces a transverse nonuniformity of the beam or pulse, with a higher index of refraction seen in the center of the beam compared to the transverse outer portions of the beam or pulse, resulting in self-focusing of the beam or pulse.

A characteristic distance for the transverse nonlinear self focusing is approximately $$L_{NSF} = \frac{z_R}{\sqrt{\frac{P(z)}{P_{NSF}} - 1}}. \quad L_{NSF} = z_R / (sqrt(P(z) - P_{NSF}) - 1)$$

where $z_R$ is the Raleigh range and is equal to $z_R = n_0 \pi R^2/\lambda$, and R is the initial beam radius. For optimal pulse compression in a given medium, $L_{NSF}$ is therefore determined by $P(0)$ and R, which should be set such that $L_{NSF} = L_{GVD}$ and longitudinal and transverse compression occur simultaneously.

In a preferred embodiment, the initial beam size and initial beam power $P(0)$ are selected so the $P_{NSF}$ threshold will be exceeded during propagation, thereby inducing non-linear effects, and the transverse self focusing and longitudinal compression occur simultaneously. Simultaneous longitudinal and transverse optical pulse compression can then occur at a chosen distance, which can be less than, equal to, or greater than the optical attenuation length.

Referring again to FIG. 1A, in an initial portion 40 of the path length L, GVD longitudinal compression increases the intensity of the negatively chirped optical pulse, triggering a non-linear transverse self-focusing effect. The intensity at any point z along the propagation direction can be represented as $$I(z) = \frac{R^2(0)T(0)}{R^2(z)T(z)} I(0) \exp\left(\frac{z}{L_{atten}}\right). \quad I(z) =$$

$(R.sup.2(0)T(0)/R.sup.2(z)T(z))I(0)\exp(z/L.sub.atten)$

In a second portion 50 of the path length, both longitudinal and transverse compression occur, further increasing the intensity of the light energy in the pulse. Convergence during nonlinear self focusing extends over a distance of only a few centimeters in a preferred embodiment.

Note that FIGS. 1A-1C are not to scale, and the transverse width is exaggerated to illustrate the NSF effect.

Figure 2:
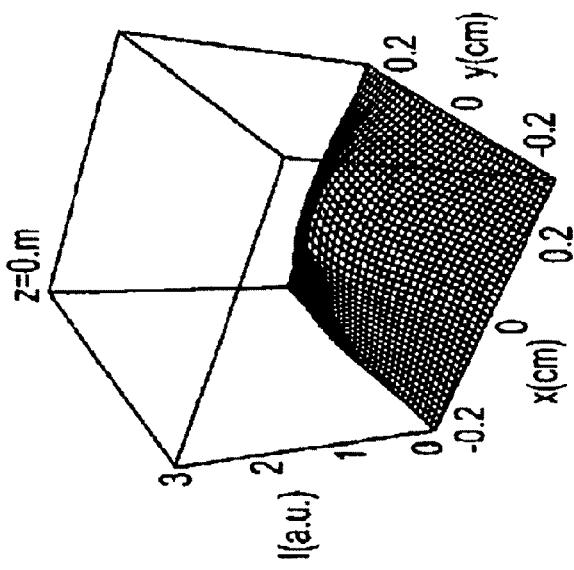
FIG. 2 shows a typical intensity profile of a laser generated optical pulse before propagation through a liquid.

FIGS. 2 and 3 illustrate the results of a computer simulation of underwater laser pulse propagation, to show the effects of group velocity dispersion and nonlinear self focusing on an optical pulse. In this example, the laser is a commercially available frequency doubled chirped pulse amplified ultrashort pulse laser, and the optical pulse has a wavelength of 400 nm, an initial pulse duration T(0) of 100 picoseconds, an initial pulse energy E(0) of 0.55 mJ, an initial beam radius R(0) of 0.29 cm, and a frequency bandwidth |.delta..omega./.omega.| of 2.5%. The medium through which the optical pulses travel is water, with a GVD parameter .beta..sub.2 of 8.times.10.sup.-28 s.sup.2/cm, a Kerr index n.sub.2 of 4.5.times.10.sup.-16 cm.sup.2/W, a linear index n.sub.0 of 1.3, and an absorption coefficient of .alpha.=0.1 m.sup.-1. FIG. 2 illustrates the intensity profile of the initial pulse, and FIG. 3 illustrates the intensity profile of the pulse after propagating through a distance of 11.4 meters. FIG. 3 shows the extreme transverse self-compression caused by the nonlinear self-focusing effect, producing an intensity level several orders of magnitude increased from the initial level.

Figure 5:
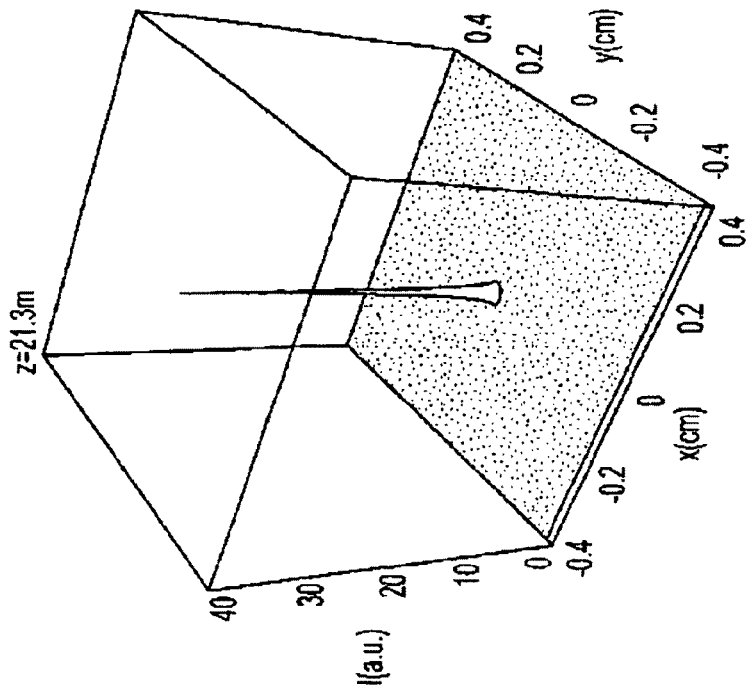
FIGS. 4 and 5 illustrate the calculated amount of pulse compression when propagating through water a distance approximately twice the attenuation length, according to an embodiment of the invention.
Figure 4:
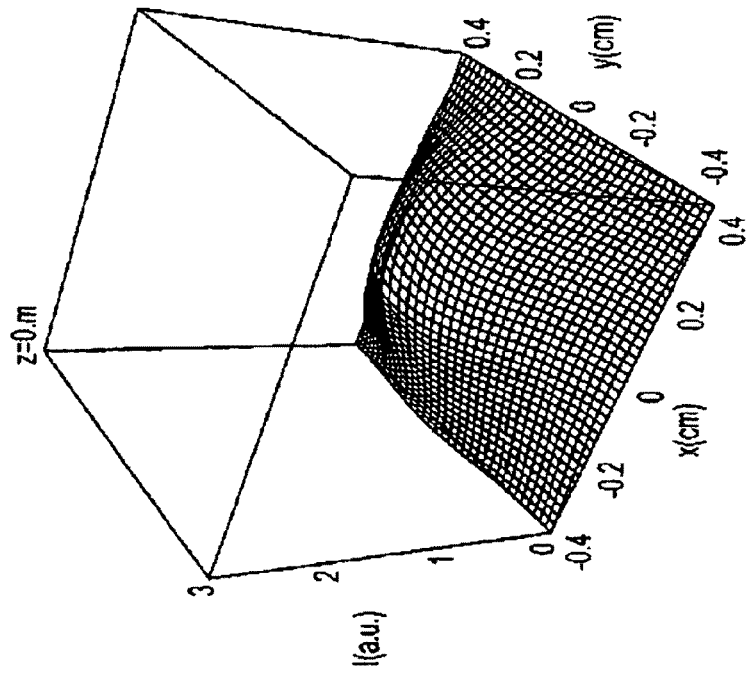

FIGS. 4 and 5 illustrate the amount of pulse compression when propagating for a distance twice the attenuation length. The initial optical pulse has a wavelength of 400 nm, an initial pulse duration T(0) of 200 picoseconds, an initial pulse energy E(0) of 2.2 mJ, an initial power level P(0) of 40 P.sub.nsf, an initial beam radius R(0) of 0.43 cm, and an initial noise amplitude of 10%. The medium through which the optical pulses travel is water, with a GVD parameter .beta..sub.2 of 8.times.10.sup.-28 s.sup.2/cm, a Kerr index n.sub.2 of 4.5.times.10-16 cm.sup.2/W, a linear index n.sub.0 of 1.3, and an absorption coefficient of .alpha.=0.1 m.sup.-1. FIG. 4 illustrates the intensity profile of the initial optical pulse, and FIG. 5 illustrates the intensity profile of the pulse after propagating through a distance of 21.3 meters.

When the intensity of the optical pulse increases sufficiently to cause laser induced breakdown in the liquid, the liquid in a small region of high intensity ionizes. A threshold intensity for laser induced breakdown (LIB), I.sub.LIB, is a function of pulse length and wavelength. In water at visible wavelengths, for a pulse length of 1 picosecond, I.sub.LIB is experimentally determined to be in the range of 10.sup.11 to 10.sup.12 W/cm.sup.2, depending on wavelength and measurement technique. Although not wishing to be bound by theory, it is noted for clarity that laser induced breakdown can have at least two mechanisms. One mechanism is multiphoton ionization by intense illumination, and is the prevailing ionization mechanism for laser pulses shorter than approximately 100 femtoseconds. A second additional, slower mechanism is avalanche ionization for significantly longer laser pulses. Avalanche ionization consists of laser excitation of a small number of "seed" free electrons, followed by collisional ionization by these electrons.

When the initial beam size is large and the initial power is sufficiently high, longitudinal compression alone can be enough to raise the intensity level of the pulse to I.sub.LIB without significant transverse compression.

For monochromatic light, GVD does not play a role and only NSF-induced transverse focusing will occur for powers above P.sub.NSF. As discussed above, when the intensity reaches I.sub.LIB, ionization will produce an acoustic pulse.

Following ionization, the plasma formed by ionization strongly absorbs laser pulse energy, causing rapid phase change (to vapor/plasma) and heating of the ionized volume. This heating occurs on laser pulse time scales, which are extremely short compared to acoustic transit times, so little or no significant expansion of the superheated vapor occurs during the laser pulse.

Figure 7:
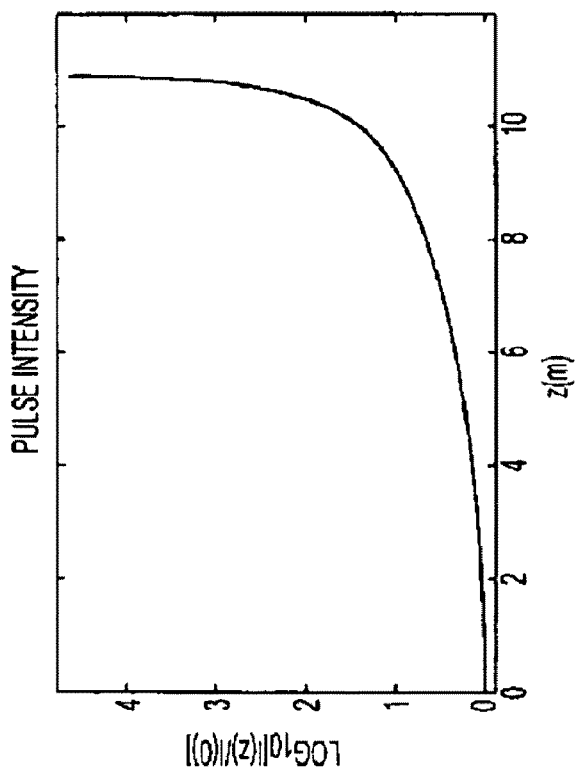
FIGS. 6 and 7 illustrate computer simulations showing the effect of pulse compression on the pulse duration, spot size, and pulse intensity.
Figure 6:
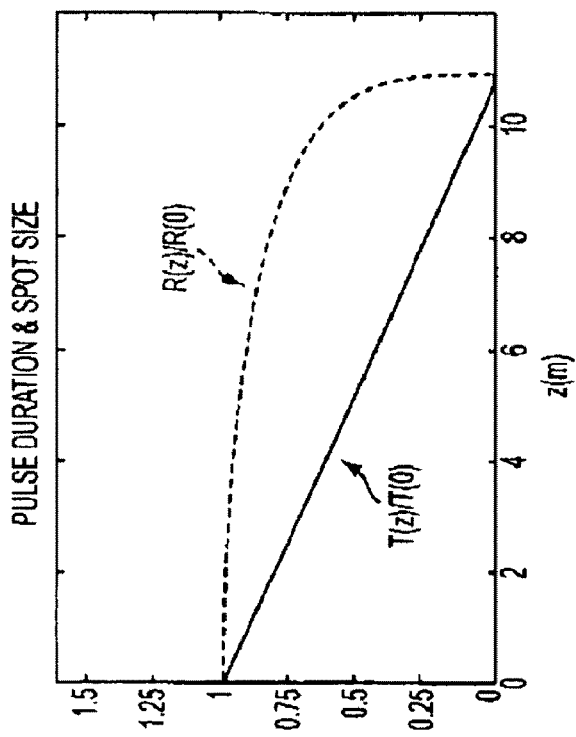

FIGS. 6 and 7 illustrate computer simulations showing the effect of pulse compression on the pulse duration, spot size, and pulse intensity. In this simulation, the initial optical pulse has a wavelength of 400 nm, an initial pulse duration T(0) of 100 picoseconds, an initial pulse energy E(0) of 1 mJ, an initial power level P(0) of 40 P.sub.nsf, an initial beam radius R(0) of 0.33 cm, frequency bandwidth |.delta..omega./.omega.| of 2.5%, and negative chirp. The water has a GVD parameter .beta..sub.2 of 8.times.10.sup.-28 s.sup.2/cm, a Kerr index n.sub.2 of 4.5.times.10-16 cm.sup.2/W, a linear index n.sub.0 of 1.3, and an absorption coefficient of .alpha.=0.1 m.sup.-1. The corresponding P.sub.nsf for 400 nm wavelength is approximately equal to 0.42 MW.

After passage of the intense electric field of the laser pulse, the ionized volume begins to recombine, leading to the optical emission of line spectra, in a relatively uniform distribution in direction. As the laser pulse is propagating through this ionized volume, it also results in self-phase modulation and white light generation, the resulting photons of which are primarily directed in the "forward" and "backward" directions, in a cone around the original propagation direction of the originating laser pulse. This will result in a broad spectrum of light being sent in a cone around the original pulse direction. White light can also be generated without sizable plasma-generation, and the original wavelength (as well as the other wavelengths present) can also be scattered/refracted into a conical pattern around the originating laser pulse direction. The resulting optical signature from the ionized volume is a combination of relatively omnidirectional line spectra, as well as a cone of white light propagating in a cone around the "forward" and "backward" directions, and roughly the laser frequency propagating in a cone in the "forward direction", both coherently and incoherently, and with different distributions of polarization. This optical signature is the illumination source we consider to operate in conjunction with the generated acoustic source. Following the rapid heating of the ionized volume, supersonic expansion and shock generation occurs more slowly, at an acoustic transit time .tau..sub.s approximately equal to d/v.sub.s, where v.sub.s is the shock speed and d is the size of the ionized volume. For typical laser energies, initial shock speed can be a few multiples of the acoustic velocity in the liquid.

The acoustic pulse length of the generated acoustic pulse can be determined by the acoustic transit time across the ionized volume in the direction of sound propagation, for a pulse that is a superposition of shock fronts generated from each initial point of supersonic expansion. Thus, larger ionized volumes, and the higher laser pulse energies required to produce them, produce longer acoustic pulses. Embodiments of the invention also include a method of controlling the duration of the acoustic pulse that accompanies the illuminating optical source by tailoring the size of the ionized volume through variation of the laser pulse energy. Additional facets of specific embodiments call for control of the optical illumination source in spectrum, direction, duration, and polarization by controlling the input laser pulse parameters discussed above.

Note that the acoustic pulse length is not necessarily the same in all directions of acoustic propagation. Embodiments of the invention include a step of adjusting the acoustic pulse by tailoring the shape of the ionized volume. For example, a laser pulse can be launched in which only GVD-induced longitudinal compression to LIB intensity occurs, thereby producing a disc-shaped ionized volume. This can produce longer acoustic pulse lengths in acoustic propagation directions parallel to the plane of the disc. Alternatively, for applications requiring only short underwater laser propagation distances without LIB range reproducibility, optical pulses with little or no frequency chirp can be generated that rely only on nonlinear self focusing effects to bring the pulse to LIB intensities.

When the laser wavelengths are in the range of 300-550 nm, acoustic generation can be accomplished remotely by underwater laser pulse propagation through distances up to or greater than the attenuation length (up to tens of meters in seawater). In contrast, when laser wavelengths are in the infrared range of about 1-11 microns, acoustic generation is confined to distances a few centimeters from the laser source. Laser induced breakdown, vaporization of the liquid, and shock generation for laser acoustic generation is also more efficient by several orders of magnitude than photo-acoustic generation via laser heating and thermal expansion of water.

The laser 10 used to generate the optical pulse can be located in air or another gaseous medium, with the optical pulses being transmitted for a distance in the air, and into the liquid medium.

In another embodiment, the laser 10 can be located in the liquid itself, with the optical pulses being transmitted through a window into the liquid. It is not necessary for the optical pulses to be generated and propagated any distance in air before being transmitted into the liquid.

Embodiments of the invention are also directed to acoustic/optical-illumination generation systems having applications in surgery, medical imaging, navigation, sonar, communications, and countermeasures for acoustically-guided undersea devices.

Figure 8:
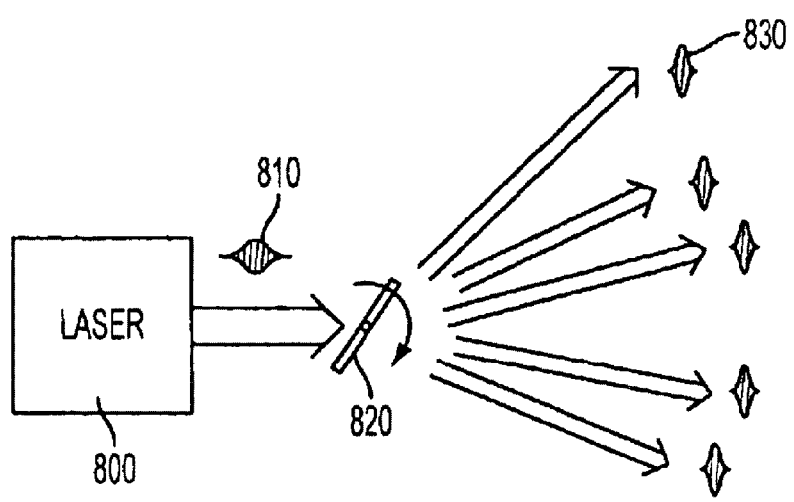
FIG. 8 illustrates a system including a repetitively pulsed laser with a moving mirror for generating multiple acoustic pulses in different locations, in accordance with one or more embodiments of the invention. In addition to the non-collinear placement of the acoustic/optical placement, the moving mirror may be held stationary or excluded if desired, in order to place the generated acoustic/optical sources in-line between the laser and/or mirror and the object of interest to be characterized.

In an embodiment illustrated in FIG. 8, repetitively pulsed laser 800 can generate optical pulses 810 that are steered by a moving mirror or other steering mechanism 820. As the mirror rotates, optical pulses steered along the arc generate acoustic/optical illumination source pulses 830 in the desired sequence and locations. These acoustic pulses can form a large acoustic aperture sonar source for high resolution acoustic imaging and multistatic acoustic scattering. The acoustic sources can be generated at a high pulse rate and timed and positioned so they form an acoustic phase front of a large aperture acoustic pulse. The simultaneous optical illumination can be used to optically image the object of interest, and once the location is known, the mirror can be held stationary to point the laser pulse in the direction of the object of interest. The optics train and laser parameters can then be adjusted to position the acoustic/optical source in the direction of the object of interest, either holding the spot steady or moving toward and/or away from the object of interest. The return optical signals can be spectrally decomposed, temporally gated, and/or compared between different polarization states and/or differing wavelengths (where in one embodiment, the different polarization states or different wavelength returns are subtracted from one another).

Figure 9:
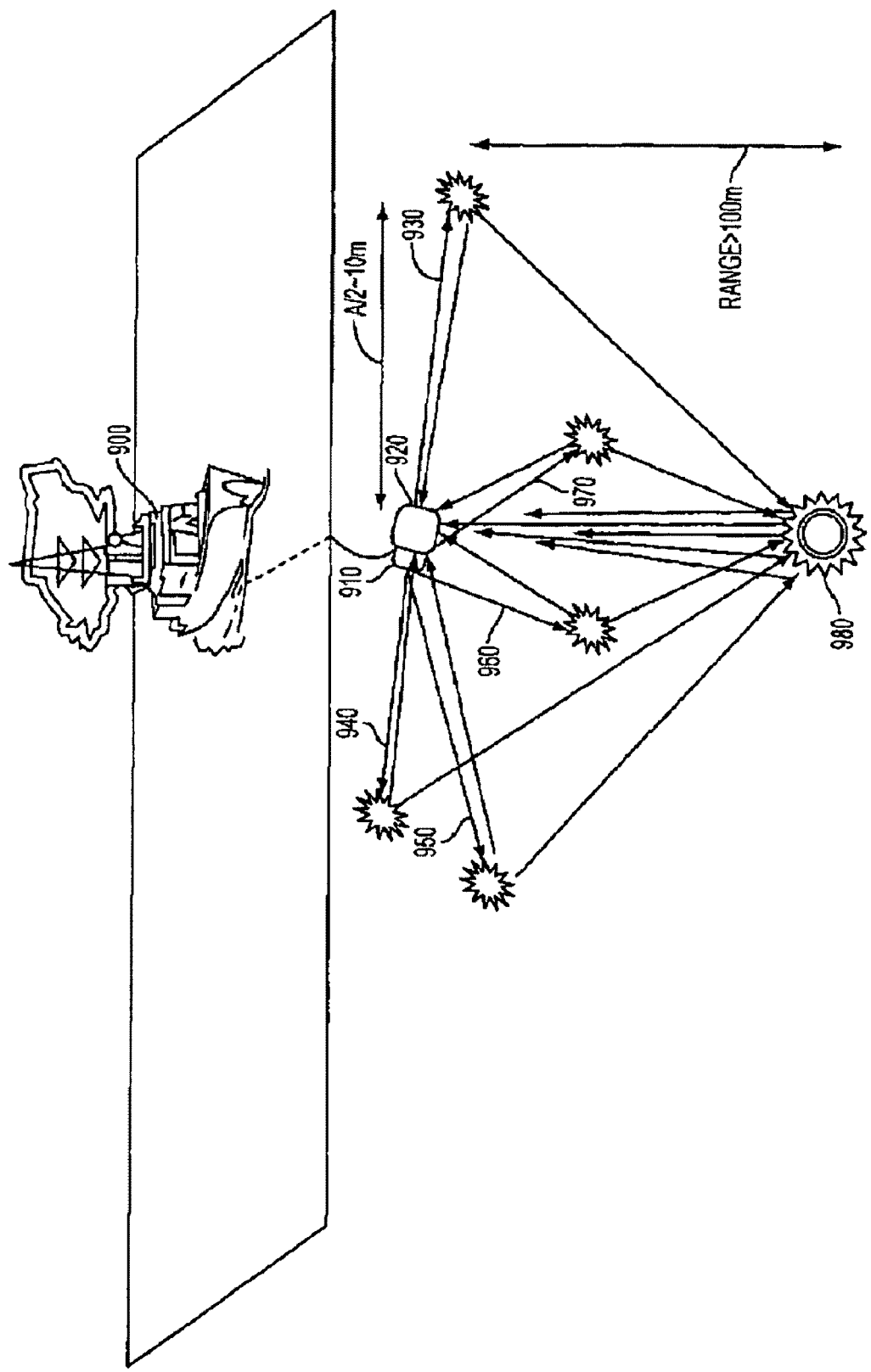
FIG. 9 illustrates a system in which a laser and acoustic detector locate and image an underwater object of interest including, but not limited to mines, unexploded ordnance, coral reefs, ocean life, submarines, features of the ocean floor and subsurface features, through acoustic/optical source/ pulse generation, in accordance with one or more embodiments of the invention. In addition to the non-collinear placement of the acoustic/optical placement, the generated acoustic/optical sources may also be in-line between the laser and object to be characterized.

As an example, FIG. 9 illustrates a system in which a laser 910 and acoustic/optical detector 920 are on an underwater platform, possibly tethered to a manned or unmanned surface ship (and/or underwater vehicle and/or stationary structure) 900. The laser generates a series of optical pulses 930, 940, 950, 960, 970, which in turn compress and generate acoustic/optical illumination sources/pulses. These acoustic and optical illumination source pulses propagate and are reflected by the object of interest 980. The acoustic/optical detector receives the reflected acoustic/optical signals from the object of interest. Because the locations of the optical pulses generated by the laser are known based on the chosen laser pulse compression range and steering mechanism setting, the system accurately determines position and reconstitutes an image of the target. The acoustic/optical detectors and/or laser can also be located on an undersea vehicle not tethered to a surface ship or a on a stationary undersea device.

Another embodiment is directed to a countermeasures system in which the acoustic/optical pulses are generated so they replicate an acoustic/visual signature of different mechanical systems of interest or to disguise the true signature of an asset to be masked.

Figure 10:
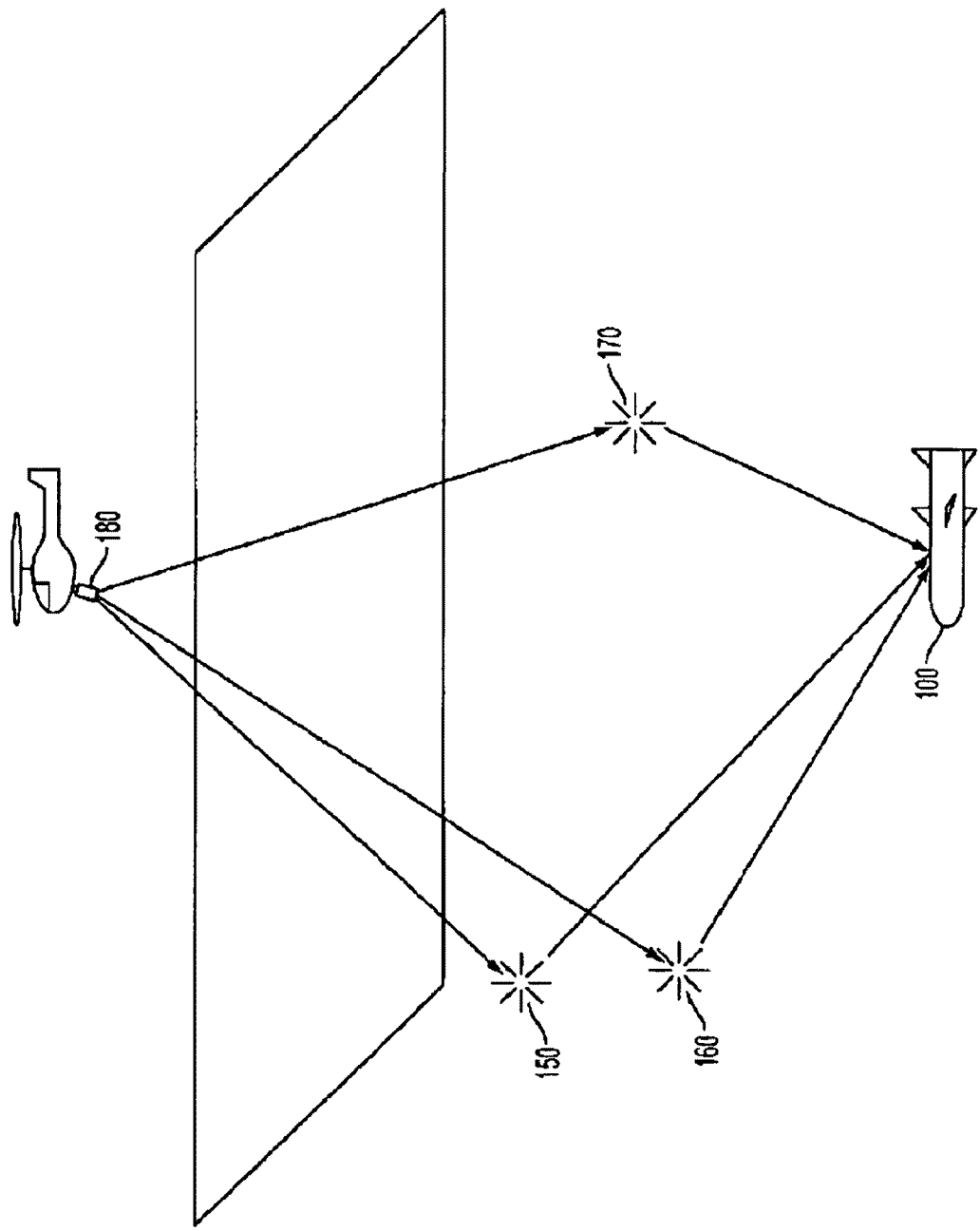
FIG. 10 illustrates a system in which acoustic/optical illumination sources/pulses are formed at expected positions and times, allowing an undersea vehicle to determine its position through triangulation, according to one or more embodiments of the invention.

Another embodiment is directed to a navigation system useful for accurate identification of the position of an undersea vehicle, and is illustrated in FIG. 10. Note that GPS is not available without an in-air antenna, so underwater vehicles can have difficulty maintaining accurate position information during lengthy underwater transits. One or more acoustic/optical signals 150, 160, and 170 are generated by a laser 180 carried by a surface ship, aircraft, or satellite at prearranged locations and timings. The AUV 100 receives the acoustic pings, and can identify its position by triangulation, analogously to a GPS device triangulating via GPS radio signals.

Regarding the optical imaging aspect of the invention, there are a number of techniques that can be fruitfully employed to yield important and accurate information about the object of interest.

The approach we describe places a source of broadband optical and acoustic energy at any desired location along a line of sight, including directly on a target. This broadband energy will come from the self-focusing and self-compression of an ultrashort laser pulse in the water, culminating in the conical emission of broadband "white" light, as well as an acoustic "snap" from the rapidly-heated medium.

Pressure (p) can be calculated by using the approximate relationship $p=P_o v(v-v_o)/(2.1)$, where v is the shock speed, $v_o$ is the sound speed in water, and $P_o$ is the water density. This can be used to determine the average pressure from the average expansion velocity of the bubble.

The amount of deposited energy can be tailored to the size and distance of the target, and can be very small since the source of white light and acoustic energy can be positioned close to the object of interest. White light generation is currently being performed in air to achieve similar objectives of imaging and spectroscopic remote sensing, and the disclosed technology employs an extension of this technology to underwater applications. Optical absorption is much smaller in the air, and this has allowed the phenomena of interest to be controlled over distances of tens of kilometers. Shorter ranges are anticipated under water.

The white light generated by the self-focused ultrashort laser pulse has been used in the air to identify different chemical species. In air, the white light illumination source can be formed several kilometers away to measure the spectrum of the returned signal back near the laser, after the white light is absorbed through the atmosphere on the way back to the point of origin. This same spectroscopic technique is anticipated to be useful under water over many meters to allow spectral identification of different compounds without a complicated and time-consuming sampling technique. This is anticipated to prove successful because of the very different spectra of most compounds of interest from that of water. Typically, aqueous solution can also hold much greater concentrations of an impurity than can air, resulting in yet stronger absorption of the returned signal (and a stronger spectral signature).

A nice broad spectrum of white light can be generated when an ultrashort pulse propagates through water. The generated spectrum can be broken up into a number of different frequency bands to enable a variety of imaging and sensing techniques, using very short and very intense white light interrogation pulses, which can be generated at points along the direction of propagation determined by the operator's choice of laser parameters.

Reflected pulses can be employed using different wavelength filters (recall the broad bandwidth of a very short pulse) and different polarization filters, as well as two different gate times. The pulse shapes at different wavelengths and polarizations are in general very reproducible, indicating that the pulses will preserve the image fidelity, and that the different images (e.g. from different polarizations, wavelengths, and time-gates) can be linearly combined (added/subtracted) to extract with great accuracy the otherwise-occluded details of the true image.

One of the most straight-forward methods to extract images is to time-gate a single camera to preferentially capture the photons that have enough time to propagate to the target and return to the measurement platform without scattering. These are called the ballistic photons, and an image captured within a short time-gate that contains the ballistic photons can generate an image of the target that is orders of magnitude stronger than an image that captures all of the scattered light.

Beyond this, a number of other techniques can be implemented when using more than one camera, including but not limited to the dual-image subtractions listed below, which have been performed to extract information, including enhancing/extracting images from otherwise murky/occluded backgrounds. Potentially interesting examples that employ dual-camera (or multiple camera) applications include:
1. Synchronized cross-polarization imaging and sensing (simultaneous spatial and temporal imaging and sensing in perpendicular polarization states) can be used to enhance materials-characterization and image-resolution. This works because the diffusely scattered light is typically polarized differently from the ballistic photons.
2. Self-calibrating fluorescence lifetime measurements can also be obtained by scanning one of the cameras in time to determine the length of a given fluorescence.
   a. Camera-1 fixed$\Rightarrow I_F(t_o)$
   b. Camera-2 varies$\Rightarrow I_F(t_0+\Delta t)$
3. Synchronized bi-spectral imagery and sensing (simultaneous spatial and temporal imaging in 2 distinct spectral bands) can extract portions of the spectrum that are preferentially reflected by the target to strongly enhance the target-image. On very fast time-scales, this technique can also be used to determine chemical reaction rates.

Underwater laser induced breakdown spectroscopy has already been demonstrated using short pulse lasers to identify a large number of elements, including Li, Na, K, Ca, Mn, and Zn at pressures up to 272 atm. Double-pulses were shown to be particularly effective (Michel et al.). This added discrimination capability using a UPL source is a powerful diagnostic when determining the physical constitution and nature of an underwater object. Once an object of interest is acoustically located, then it can be interrogated using the underwater LIBS technique, using one or more pulses at each point for the best results.

Beyond the optical methods described above, broad, high-frequency acoustic interrogation will further aid in identifying a material in question. Dolphins identify materials by bouncing broad acoustic signals, centered around roughly 180 kHz, off of their targets and listening to the echoes. We anticipate a greatly enhanced discrimination ability using the much higher and much broader acoustic signature produced with the ultrashort pulse laser cavitation. This serves as an extension of the acoustic-identification phenomena already used in nature, and can be employed in a variety of applications.

In air, spectroscopy has been performed using the backscattered white light to measure various atmospheric constituents. This technique can be extended to underwater environmental sampling. We foresee its utility in determining the presence of trace explosives, combustion products, pollutants, and hazardous materials.

The technique will result in improved acoustic and optical fidelity with which targets can be resolved, using much lower and more localized power requirements. We anticipate a sufficient concentration of acoustic and optical energy on target, and very little not on target. Improved speed with which high-fidelity images and spectra can be obtained of the target, including spectral characterization of a water-volume of interest. This is anticipated to be nearly instantaneous, affording immediate identification of target material and hazardous chemicals/materials in the water. Important targets and/or materials can also be identified through turbid water, demonstrating a new and valuable capability.

The disclosed invention extends the UPL remote-sensing techniques already being contemplated in air, and will expedite and improve both qualitative and quantitative characterization of underwater objects and chemicals present in the ocean environment. Chemical analyses which can currently require hours or days will be performed spectrally, allowing for immediate identification of hazards and response to remediate them. Regarding underwater objects of interest, the disclosed invention will dramatically increase both the accuracy and speed of target identification. Knowing that a target is made of wood, steel, or Aluminum (or any other constitution) will result in a much faster determination of how to deal with it. Knowing that the surrounding water does or does not contain trace concentrations of explosives, fuel, or other chemicals or hazardous material will also dramatically increase the accuracy of how to deal with the target of interest. This spectral information, coupled with the accompanying high-fidelity multi/hyper-spectral and acoustic images will allow for faster and more accurate responses, as well as far less frequent categorization of objects as "unknown", relegated to further investigation in the unknown future. In addition to benefiting current Government operations, this ability will also help in the identification and removal of unexploded ordnance and decrease the acoustic and optical energy required in such characterization, thereby reducing the environmental effect of these operations.

There are a number of areas that can strongly benefit from this technique, including aquaculture enterprises, which have an extremely strong interest in real-time tracking of the constitution of their water column. This is necessary to maintain quality control and to abide by Government regulations. These capabilities will be helpful anywhere sampling is currently required, such as waste-water management and recreational beach usage. As the world's population continues to grow, these areas are becoming increasingly problematic and will be able to benefit from real-time, remote, non-invasive sampling capabilities.

We envision a system that will allow immediate optical, acoustic, and spectral characterization of objects of interest, as well as immediate spectral characterization of trace compounds in the water. These applications are of great importance with respect to: swimmer detection; unexploded ordnance; mapping the ocean terrain; identifying vehicles (keeping in mind regular exercises for undersea warfare and other war games); Maritime Domain Awareness; efforts employing multiple cameras to build on the single-camera applications/capabilities, including comparison/subtraction of images filtered with different polarizers and/or spectral filters.

Many of these techniques pertain directly to medical imaging which is also a preferred embodiment. The body structures are made up of: soft tissue resembling water; air in the stomach, lungs, and intestines; and hard tissues, such as bone. Biological tissues can also be probed/imaged both optically and acoustically using the disclosed invention. The longer wavelengths (IR) are typically best for optically penetrating the soft body tissues. In this case, the body can be optically probed and mapped to identify locations that require attention, possibly from acoustic energy or LIBS. The optical probing can again take place, temporally gating the pulse returns to eliminate scatter and/or also comparing/differencing different polarization states and/or spectral windows. Conversely, as with the underwater case, the body can first be mapped acoustically to identify areas of interest and then optically mapped, based on the acoustic guidance.

Candidate Claims will include, but are not limited to combinations of the various diagnostic capabilities afforded by the ultrashort pulse laser interactions with the liquid, including: the high-frequency, broad-spectrum acoustic signature that comes from the rapid expansion of the vaporized liquid; the laser-induced breakdown spectrum of the liquid itself and of a surface of interest; the broad-spectrum, conically-directed white-light generated by the laser focus; time-gated imaging of the target, whose distance can be determined by the acoustic return; spectral comparison using filters and the broadband illumination; polarimetric comparison, using the differences in polarization of the ballistic photons from the scattered ones.

Obviously, many modifications and variations of the present invention are possible in light of the above teachings. It is therefore to be understood that the claimed invention may be practiced otherwise than as specifically described.

Another embodiment includes a focusing lens near the laser, where the optical pulse begins its underwater propagation. Initial optical pulse intensity is limited by filamentation instabilities. The lens can serve to collect and transversely focus more pulse energy than would otherwise be possible given this intensity limit and the collimated beam size required for non-linear transverse self-focusing at a given distance.

The invention has been described with reference to certain preferred embodiments. It will be understood, however, that the invention is not limited to the preferred embodiments discussed above, and that modification and variations are possible within the scope of the appended claims.

What is claimed is:

1. A method for characterizing an immersed object comprising:
   (A) generating a plurality of acoustic and optical illumination sources in a liquid proximate the object, and
   (B) measuring and analysing the returned acoustic and optical signals.

2. The method according to claim 1, wherein the liquid is water.

3. The method according to claim 1, wherein the liquid is seawater.

4. The method according to claim 1, wherein the sources are generated from a plurality of laser generated optical pulses.

5. The method according to claim 4, without lens focusing of the optical pulses.

6. The method according to claim 4, with lens focusing of the optical pulses.

7. The method according to claim 4, wherein the optical pulses have a wavelength between 300 and 500 nanometers.

8. The method according to claim 4, wherein the optical pulses have a wavelength less than 11 microns.

9. The method according to claim 4, wherein the optical pulses travel through the liquid for distances of at least one meter.

10. The method according to claim 9, wherein the sources are generated at a distance of between 1 and 50 meters from the object.

11. The method according to claim 4, wherein the optical pulses are negatively chirped optical pulses.

12. The method according to claim 4, wherein the optical pulses are negatively chirped optical pulses, and the liquid has a positive optical group velocity dispersion parameter $\beta_2$.

13. The method according to claim 4, wherein the optical pulses are positively chirped optical pulses.

14. The method according to claim 4, wherein the optical pulses are positively chirped optical pulses, and the liquid has a negative optical group velocity dispersion parameter $\beta_2$.

15. The method according to claim 4, wherein the optical pulses are monochromatic optical pulses.

16. The method according to claim 4, wherein the optical pulses are broadband optical pulses without chirp.

17. The method according to claim 4, wherein the optical pulses have a wavelength varying effectively linearly with time.

18. The method according to claim 1, wherein the liquid is water, including sea water, and the optical pulses are generated under water.

19. The method according to claim 1, wherein the liquid is water, including sea water, and the optical pulses are generated in air and are transmitted into the water.

20. The method according to claim 1, wherein the optical signal analysis consists of manipulating different polarization states of the returned optical signals, in the form of comparing and differencing them.

21. The method according to claim 1, wherein the optical signal analysis consists of manipulating different spectral bands of the returned white light optical signals, in the form of comparing and adding them.

22. The method according to claim 1, wherein the optical signal analysis consists of time-gating the images in order to compare and add them in order to generate a 3D image of the target of interest.

23. The method according to claim 1, wherein the optical signal analysis consists of measuring the laser induced breakdown spectrum of the object's laser-ionized material surface, ionized by one or more shots at each ionized position to assess the object's surface material composition at that position.

24. A method for characterizing a volume of liquid by generating a serial plurality of acoustic and optical illumination sources in a liquid, the method comprising: trnasmitting a serial plurality of laser-generated optical pulses through the liquid; the optical pulses reaching $I_{LIB}$ at optically specified locatinos, through pulse compression and ionizing a liquid volume, thereby generating a serial plurality of acoustic and optical illumination source pulses, wherein the pulse compression is achieved through at least one of a) optical group velocity dispersion induced longitudinal compression of a frequency chirped optical pulse and b) transverse self focusing via a nonlinear optical Kerr effect; rastering throughout the volume; and then measuring and analysing the returned line spectra of the laser induced breakdown to verify the composition of the water and analysing the returned acoustic signals to verify the location of the optical sources.

25. A method for characterizing a volume of liquid by generating a serial plurality of acoustic and optical illumination sources in a liquid, the method comprising: transmitting a serial plurality of laser-generated optical pulses through the liquid; the optical pulses reaching $I_{LIB}$ at optically specified locations, through pulse compression and ionizing a liquid volume, thereby generating a serial plurality of acoustic and optical illumination source pulses, wherein the pulse compression is achieved through at least one of a) optical group velocity dispersion induced longitudinal compression of a frequency chirped optical pulse and b) transverse self focusing via a nonlinear optical Kerr effect; rastering throughout the volume; and then measuring and analysing the returned absorption spectra of the conical emission of white to verify the composition of the water and analysing the returned acoustic signals to verify the location of the optical sources.

26. A method for acoustically and optically imaging living tissue by generating a serial plurality of acoustic and optical illumination sources at the surface of the body, capable of penetrating the tissue, allowing for optiacal and acoustic return signals to be gated and read to reconstruct the tissue geometry.

27. A method for characterizing an immersed object comprising:
   (A) generating a plurality of acoustic and optical illumination sources in a liquid proximate the object, and
   (B) measuring and analysing the returned optical signals.

28. The method according to claim 27, wherein the optical signal analysis consists of manipulating different polarization states of the returned optical signals, in the form of comparing and differencing them.

29. The method according to claim 27, wherein the optical signal analysis consists of manipulating different spectral bands of the returned white light optical signals, in the form of comparing and adding them.

30. The method according to claim 27, wherein the optical signal analysis consists of time-gating the images in order to compare and add them in order to generate a 3D image of the target of interest.

31. The method according to claim 27, wherein the optical signal analysis consists of measuring the laser induced breakdown spectrum of the object's laser-ionized material surface, ionized by one or more shots at each ionized position to assess the object's surface material composition at that position.

* * * * *